United States Patent [19]

Kitagawa et al.

[11] Patent Number: 4,841,076
[45] Date of Patent: Jun. 20, 1989

[54] BENZOPYRAN DERIVATIVES

[75] Inventors: Masayuki Kitagawa; Makoto Tanaka, both of Tokyo, Japan

[73] Assignee: Daiichi Seiyaku Co., Ltd., Japan

[21] Appl. No.: 58,105

[22] Filed: Jun. 4, 1987

[30] Foreign Application Priority Data

Jun. 4, 1986 [JP] Japan .............................. 61-129420

[51] Int. Cl.⁴ .......................................... C07D 311/22
[52] U.S. Cl. ..................................... 549/401; 549/403
[58] Field of Search ................................ 549/401, 403

[56] References Cited

U.S. PATENT DOCUMENTS 3,864,362  2/1975  Feuer et al. ......................... 549/403
4,644,012  2/1987  Tsuda et al. ........................ 549/403

FOREIGN PATENT DOCUMENTS

A666541  11/1965  Belgium .
1193511   5/1965  Fed. Rep. of Germany .
1210882   2/1966  Fed. Rep. of Germany .
2100692   3/1972  France .
47-46067  11/1972  Japan ................................... 549/403
803372   10/1958  United Kingdom .

OTHER PUBLICATIONS

Chemical Abstracts, vol. 60, 1964, column 1709b–d.
Journal of the Chemical Society, vol. 12, 1962, pp. 5121–5125, chapter 986.
Chemical Abstracts, vol. 78, 1973, p. 345, Ref. No. 4125c.

Primary Examiner—Nicky Chan
Attorney, Agent, or Firm—Sughrue, Mion, Zinn, Macpeak & Seas

[57] ABSTRACT

A benzopyran derivative represented by formula

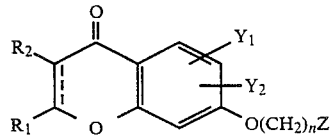

wherein:
R₁ and R₂ each represents a hydrogen atom, a lower alkyl group, a substituted or unsubstituted cyclic alkyl group, a mono- or di-lower alkylamino group, a substituted or unsubsituted cyclic amino group, a substituted or unsubstituted aryl group, or a substituted or unsubstituted aralkyl group;

$Y_1$ and $Y_2$ each represents a hydrogen atom, a lower alkyl group, a halogen atom or a trihalomethyl group;

Z represents a caroxyl group, a lower alkoxy-carbonyl group, a tetrazolyl group, a hydroxyl group or —CONR₃R₄ wherein R₃ and R₄ each represents a hydrogen atom or a lower alkyl group;

n represents an integer of from 1 to 6; and the bond between the 2- and 3-positions represents a single bond or a double bond;

provided that a combination wherein $Y_1$, $Y_2$, and $R_2$ each represents a hydrogen atom, $R_1$ represents a phenyl group, n represents 1, Z represents a carboxyl group or an alkoxycarbonyl group, and the bond represents a double bond, and a combination wherein $Y_1$, $Y_2$, and $R_1$ each represents a hydrogen atom, $R_2$ represents a phenyl group, n represents 1, Z represents a carboxyl group or an alkoxy-carbonyl group, and the bond represents a double bond are excluded, and pharmaceutically acceptable salts thereof are disclosed. These compounds have uricosuric activity, diuretic activity and antihypertensive activity, and are useful as pharmaceuticals.

6 Claims, No Drawings

BENZOPYRAN DERIVATIVES

FIELD OF THE INVENTION

This invention relates to benzopyran derivatives and salts thereof which have uricosuric activity, diuretic activity, and antihypertensive activity and are, therefore, useful as pharmaceuticals.

BACKGROUND OF THE INVENTION

Known compounds having diuretic and uricosuric activities include tienilic acid ([2,3-dichloro-4-(2-thenoyl)phenoxy]acetic acid) as disclosed in U.S. Pat. No. 3,758,506, indacrinone ([6,7-dichloro-2,3-dihydro-2-methyl-1-oxo-2-phenyl-1H-inden-5-yl]oxy]acetic acid) as disclosed in *Journal of Medicinal Chemistry*, Vol. 21, 437-442 (1978), and the compounds disclosed in Japanese Patent Application (OPI) Nos., 500573/85, 764948/83 and 102522/84 (the term "OPI" as used herein means "unexamined published Japanese patent application"). However, these compounds are unsatisfactory in uricosuric, diuretic, and antihypertensive activities.

Also, a benzopyran derivative is reported in *Arzneim.-Forsch.*, Vol. 30, 2126 (1980) as having diuretic and saluretic activities, but this compound has no uricosuric activity.

SUMMARY OF THE INVENTION

As a result of extensive investigations to solve the above-described problem, it has now been found that a novel compound represented by formula (I) shown below and salts thereof exhibit excellent uricosuric, diuretic, and antihypertensive activities.

Formula (I) is represented by

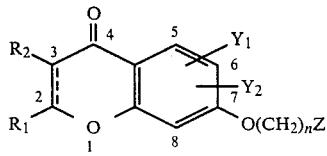

wherein:

$R_1$ and $R_2$ each represents a hydrogen atom, a lower alkyl group, a substituted or unsubstituted cyclic alkyl group, a mono- or di-lower alkylamino group, a substituted or unsubstituted cyclic amino group, a substituted or unsubstituted aryl group, or a substituted or unsubstituted aralkyl group;

$Y_1$ and $Y_2$ each represents a hydrogen atom, a lower alkyl group, a halogen atom or a trihalomethyl group;

Z represents a carboxyl group, a lower alkoxycaronyl group, a tetrazolyl group, a hydroxyl group or —$CONR_3R_4$ wherein $R_3$ and $R_4$ each represents a hydrogen atom or a lower alkyl group;

n represents an integer of from 1 to 6; and the bond===between the 2- and 3-positions represents a single bond or a double bond;

provided that a combination wherein $Y_1$, $Y_2$, and $R_2$ each represents a hydrogen atom, $R_1$ represents a phenyl group, n represents 1, Z represents a carboxyl group or an alkoxycarbonyl group, and the bond=== represents a double bond, and a combination wherein $Y_1$, $Y_2$, and $R_1$ each represents a hydrogen atom, $R_2$ represents a phenyl group, n represents 1, Z represents a carboxyl group or an alkoxycarbonyl group, and the bond===represents a double bond are excluded.

DETAILED DESCRIPTION OF THE INVENTION

In formula (I), the term "lower alkyl group" as used for $R_1$, $R_2$, $Y_1$, $Y_2$, $R_3$, and $R_4$ means an alkyl group containing from 1 to 6 carbon atoms and includes methyl, ethyl, propyl, isopropyl, n-butyl, isobutyl, t-butyl groups and the like. The term "cyclic alkyl group" as used for $R_1$ or $R_2$ includes cyclopropyl, cyclobutyl cyclopentyl, cyclohexyl, cycloheptyl groups and the like, and the cyclic groups may have one or more substituents. Substituents on the cyclic alkyl group include a lower alkyl group and the like. Alkyl groups in the di-lower alkylamino group for $R_1$ or $R_2$ may be the same or different. The cyclic amino group of $R_1$ or $R_2$ includes 1-pyrrolidinyl, 1-piperidinyl, 1-piperazinyl, 4-morpholinyl, 4-thiomorpholinyl, 1-homopiperazinyl groups and the like, and the cyclic amino group may have one or more substituents. Substituents on the cyclic amino group include a lower alkyl group and the like. The aryl group includes phenyl, naphthyl, biphenyl groups and the like, and the aryl group may have one or more substituents. Substituents on the aryl group include a hydroxyl group, a halogen atom, a lower alkyl group, a lower alkoxy group, and the like. The aralkyl group includes benzyl, phenylethyl, naphthylmethyl, naphthylethyl, biphenylmethyl, phenylpropyl groups and the like, and the aralkyl group may have one or more substituents. Substituents on the aralkyl group include a hydroxyl group, a halogen atom, a lower alkyl group, a lower alkoxy group, and the like. These substituents may be bonded to either the aryl moiety or the alkylene moiety of the aralkyl group. When the aforesaid cyclic alkyl, cyclic amino, aryl or aralkyl group has two or more substituents, such substituents may be the same or different. The halogen atom includes fluorine, chlorine, bromine, and iodine atoms.

The compound of formula (I) can form alkali metal or alkaline earth metal salts, e.g., a sodium salt, a potassium salt, a calcium salt, a magnesium salt, etc., an ammonium salt, and amine salts, e.g., an N-methylglucamine salt, an ethanolamine salt, etc., in cases where Z represents a carboxyl group or a tetrazolyl group. Also, the compound of formula (I) can form acid addition salts with inorganic acids, e.g., hydrochloric acid, sulfuric acid, etc., or organic acids in cases where $R_1$ or $R_2$ represents a mono- or di-lower alkylamino group or a cyclic amino group.

Of the compounds of formula (I), a preferred class of compounds is represented by the following formula (I').

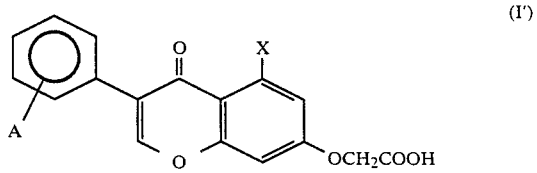

wherein X represents a halogen atom, and A represents a hydrogen atom, a halogen atom, a lower alkyl group or a lower alkoxy group.

A more preferred class of compounds is represented by the above formula (I') wherein X represents a chlorine atom and A represents a hydrogen atom, a 2-chlorine atom, a 2-methyl group or a 4-methoxy group.

The compounds of the present invention can be prepared by one of the following processes (a) to (e), depending on the definition of the substituents in the compounds of formula (I).

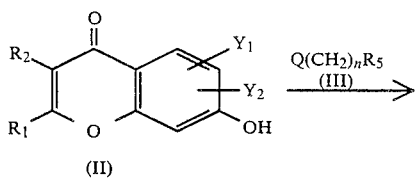
(a)

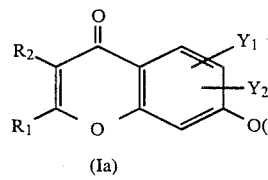
(Ia)

In the above formulae, $R_1$, $R_2$, $Y_1$, $Y_2$, and n are as defined above; $R_5$ represents a lower alkoxycarbonyl group or a hydroxyl group; and Q represents a halogen atom.

The compound of formula (Ia) can be prepared by reacting the compound of formula (II) with the compound of formula (III) in an amount of from 1 to 1.5 moles per mole of the compound of formula (II), in an organic solvent, such as dimethylformamide and acetone, in the presence of a carbonate or hydroxide of an alkali metal or alkaline earth metal, e.g., potassium carbonate, sodium hydroxide, potassium hydroxide, etc. in an amount of from 1 to 2 moles per mole of the compound of formula (II). The reaction can be carried out at from room temperature (e.g., 1° to 30° C.) to about 100° C. for 0.5 to 24 hours. The solvent is generally used in an amount of from 5 to 100 times (by weight) the amount of the compound of formula (II).

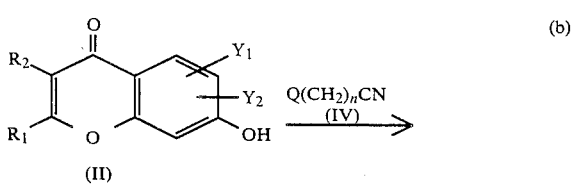
(b)

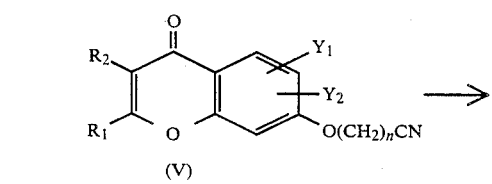
(V)

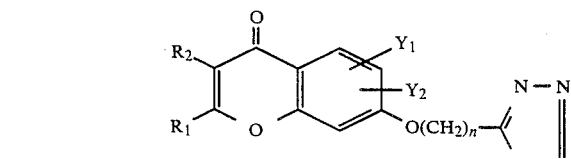
(Ib)

In the above formulae, $R_1$, $R_2$, $Y_1$, $Y_2$, n, and Q are as defined above.

The compound of formula (II) can be reacted with the compound of formula (IV) in a known manner as described in *Journal of Medicinal Chemistry*, Vol. 21, 437–442 (1978) to prepare the compound of formula (V). Then, the compound of formula (V) can be reacted with a metal salt of hydrogen azide, e.g., sodium azide, in the presence of ammonium chloride at from 50° to 100° C. for 0.5 to 24 hours in an organic solvent, e.g., dimethylformamide, to prepare the compound of formula (Ib). The metal salt of hydrogen azide and ammonium chloride can be used at a molar ratio of from 1 to 1.5 moles per mole of the compound of formula (V). The solvent is generally used in an amount of from 5 to 100 times (by weight) the amount of the compound of formula (V).

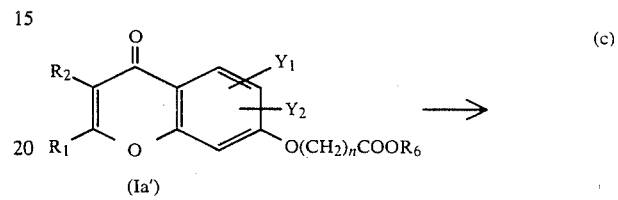
(c)

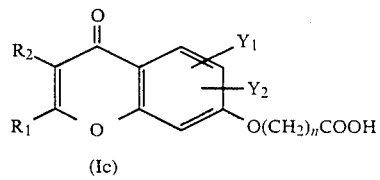
(Ic)

In the above formulae, $R_1$, $R_2$, $Y_1$, $Y_2$, and n are as defined above; and $R_6$ represents a lower alkyl group.

The compound of formula (Ic) can be prepared by reacting the compound of formula (Ia') with an inorganic base, such as a hydroxide of an alkali metal or alkaline earth metal, in water or a mixed solvent of water and an organic solvent, e.g., ethanol, methanol, dioxane, dimethylformamide, etc. The reaction can be carried out at from room temperature to 50° C. for 0.5 to 24 hours. The solvent is generally used in an amount of from 5 to 10 times (by weight) the amount of the compound of formula (Ia'). The inorganic base can be used at a molar ratio of from 1 to 10 moles per mole of the compound of formula (Ia').

The compound of formula (Ic) can also be prepared by reacting the compound of formula (Ia') with boron tribromide in an organic solvent, e.g., dichloroethane, etc. at from 0° to 100° C. for 0.5 to 12 hours. The solvent is generally used in the same amount as that described above. The boron tribromide can be used at a molar ratio of from 1 to 10 moles per mole of the compound of formula (Ia').

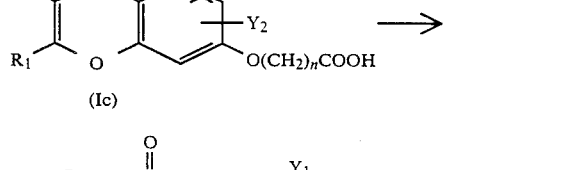
(d)

(Ic)

(Id)

-continued

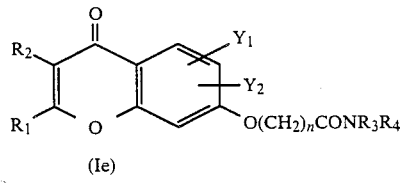
(Ie)

In the above formulae, $R_1$, $R_2$, $Y_1$, $Y_2$, $R_3$, $R_4$, n and Q are as defined above.

The compound of formula (Ic) can be reacted with a halogenating agent, e.g., thionyl chloride in the absence of solvent or in a solvent, e.g., chloroform, dichloromethane, 1,2-dichloroethane, etc., at from room temperature to 100° C. for 30 minutes to 12 hours to prepare the compound of formula (Id). The solvent is generally used in an amount of from 5 to 100 times (by weight) the amount of the compound of formula (Ic). The halogenating agent can be used in an equimolar amount or a molar excess amount to the compound of formula (Ic).

The compound of formula (Id) thus obtained can be reacted with the amine $NHR_3R_4$ in an organic solvent, e.g., benzene, etc., from room temperature to 50° C. for 1 to 12 hours to prepare the compound of formula (Ie). The solvent is generally used in an amount of from 5 to 100 times (by weight) the amount of the compound of formula (Id). The amine $NHR_3R_4$ can be used at a molar ratio of from 1 to 10 moles per mole of the compound of formula (Id).

-continued

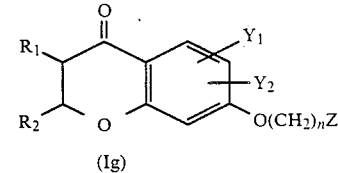
(Ig)

In the above formulae, $R_1$, $R_2$, $Y_1$, $Y_2$, Z, and n are as defined above.

The compound of formula (Ig) can be prepared by catalytic reduction of the compound of formula (If) in an appropriate organic solvent, e.g., methanol, ethanol, etc., in the presence of a catalyst, e.g., platinum (IV) oxide, palladium charcoal etc., in accordance with a known process, as described in *Jikken Kagaku Koza*, Vol. 21 (Second Volume), 175. The catalytic reduction can be carried out at from room temperature to 50° C. until the absorption of of hydrogen atom is completed. The solvent is generally used in an amount of 5 to 200 times (by weight) the amount of the compound of formula (Ie). The catalyst can be used in an amount of from 0.01 to 0.1 part by weight per part by weight of the compound of formula (Ie).

The compound of formula (II) which is used as a starting compound in the above-described reactions can be prepared by the following processes (f) and (g), according to the definition of substituents in the compounds of formula (II).

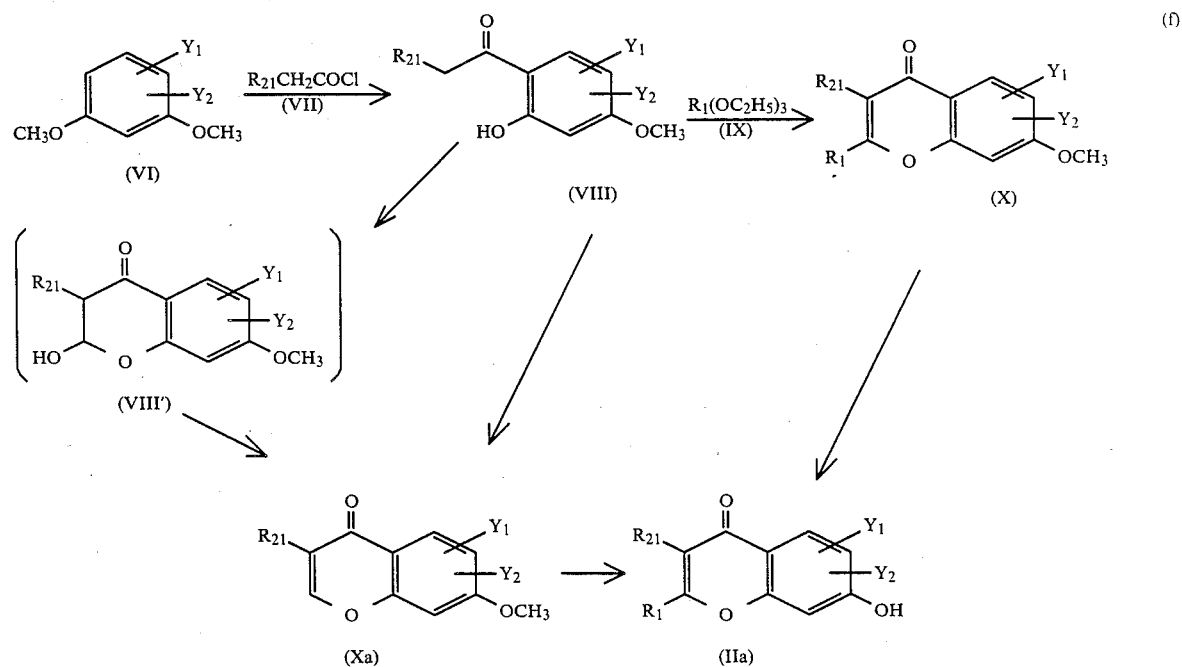
(f)

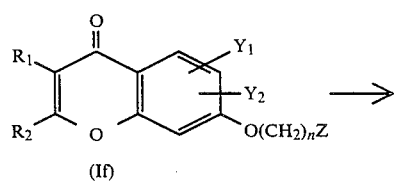
(e)

In the above formulae, $R_1$, $Y_1$, and $Y_2$ are as defined above; and $R_{21}$ represents a lower alkyl group, a substituted or unsubstituted cyclic alkyl group, a substituted or unsubstituted aryl group, or a substituted or unsubstituted aralkyl group.

The compound of formula (VI) can be reacted with the compound of formula (VII) in an organic solvent, e.g., 1,2-dichloroethane, in the presence of anhydrous aluminum chloride to prepare the compound of formula (VIII). The compound of formula (VIII) can be then reacted with the compound of formula (IX) in the presence of pyridine and piperidine in accordance with a known process, as described in *Chemical Abstracts*, Vol. 46, 500d, to prepare the compound of formula (X). The compound of formula (X) wherein $R_1$ is a hydrogen atom, i.e., the compound of formula (Xa) can also be prepared by reacting the compound of formula (VIII) with ethy formate in the presence of sodium hydride or sodium in accordance with a known process, as described in *Chemical Abstracts*, Vol. 49, 13981a or *Journal of Society India Research*, Vol. 113, 347–348 (1952). In this reaction, by-product of formula (VIII') sometimes produces. The by-product of formula (VIII') can be converted into the compound of formula (Xa) by heating at from about 140° to about 170° C. The thus obtained compound of formula (X) can then be reacted with anhydrous aluminum chloride in a nonpolar organic solvent, e.g., benzene, at from about 50° to about 100° C. to prepare the compound of formula (IIa).

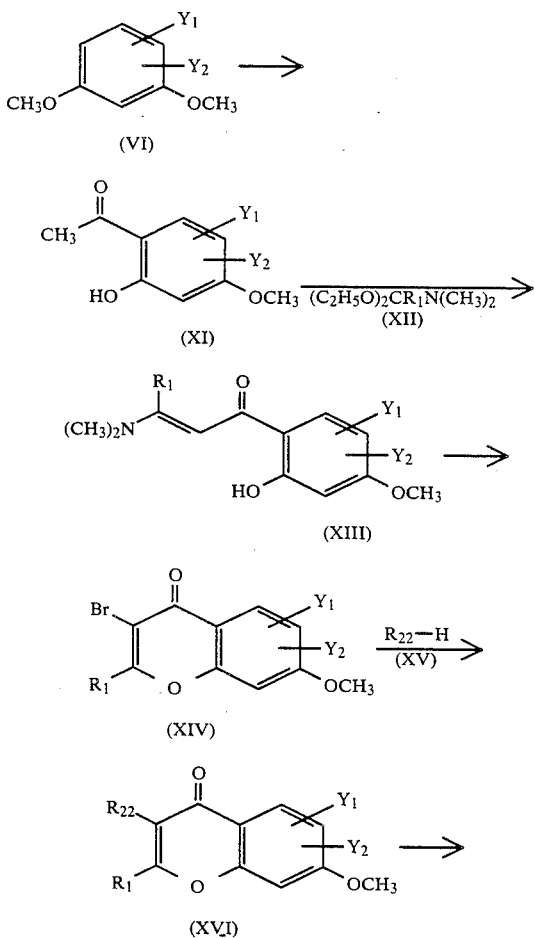

In the above formulae, $R_1$, $Y_1$, and $Y_2$ are as defined above; and $R_{22}$ represents a mono- or di-lower alkyl- amino group or a substituted or unsubstituted cyclic amino group.

The compound of formula (VI) can be reacted with acetyl chloride in the presence of anhydrous aluminum chloride to prepare the compound of formula (XI), which can be then reacted with the compound of formula (XII) in accordance with a known process, as described in *Synthesis*, Vol. 11, 901–903 (1979) to prepare the compound of formula (XIII). The prepared compound (XIII) can be reacted with bromine to obtain the compound of formula (XIV), which can be then reacted with the compound of formula (XV) to prepare the compound of formula (XVI). The compound of formula (XVI) can be reacted with hydrobromic acid to prepare the compound of formula (IIb).

The compound of formula (VII) used as a starting compound in process (f) can be prepared by reacting a compound of formula (XVII) with thionyl chloride as shown below.

$$R_{21}CH_2COOH \rightarrow (VII) \qquad (XVII)$$

wherein $R_{21}$ is as defined above.

The compound of formula (I) and a salt thereof of the present invention are excellent in uricosuric activity, diuretic activity, and antihypertensive activity and are, therefore, useful as pharmaceuticals.

The pharmacological activities of the compound of the present invention are described in the following experiments. In these experiments, the test compounds used are as follows.

(a): [(5-Chloro-4-oxo-3-phenyl-4H-1-benzopyran-7-yl)oxy]acetic acid (b): [(5-Methyl-4-oxo-3-phenyl-4H-1-benzopyran-7-yl)oxy]acetic acid (c): {[5-Chloro-3-(2-chlorophenyl)-4-oxo-4H-1-benzopyran-7-yl]oxy}acetic acid (d): {[5-Chloro-3-(2-methylphenyl)-4-oxo-4H-1-benzopyran-7-yl]oxy}acetic acid (e): [(3-Benzyl-5-chloro-4-oxo-4H-1-benzopyran-7-yl)oxy]acetic acid (1) Diuretic Activity and Natriuretic Activity:

Male rats weighing 150 to 250 g were fasted overnight and, the next morning, orally administered with either (1) 25 ml/Kg of physiological saline (control group) or (2) a test compound which was suspended in 0.5 wt % carboxymethylcellulose. Urine after dosing was collected for 5 hours, and urinary volume and sodium concentration were measured. Each parameter was calculated by subtracting the value of the control group from that of the test group. The results obtained are shown in Table 1 below.

TABLE 1

| Test Compound | Number of Animals | Dose (mg/Kg) | Increase in Urinary Output ($\Delta$ml/Kg) | Increase in Urinary $Na^+$ ($\Delta\mu Eq$) |
|---|---|---|---|---|
| (a) | 7 | 300 | 51.8** | 1220** |
| (b) | 7 | 300 | 23.6** | 987** |
| (c) | 7 | 300 | 41.0** | 1015** |
| (d) | 7 | 300 | 49.6** | 1196** |
| (e) | 7 | 300 | 37.9** | 967** |
| Tienilic acid | 7 | 300 | 10.2* | 353.4** |

*$P < 0.05$ vs. Control
**$P < 0.01$ vs. Control

As is apparent from the Table 1, the compounds of the present invention exhibited higher diuretic and natriuretic activities as compared with tienilic acid.

(2) Uricosuric Activity:

Male rats weighing 150 to 250 g were fasted overnight and, the next morning, orally administered with either (1) 25 ml/Kg of physiological saline (control group) or (2) a test compound which was suspended in 0.5 wt % carboxymethylcellulose. After 60 minutes from the administration of the test compound, urine over a period of 30 minutes was collected. Thereafter, blood was taken from the arotid artery under anesthesia, and uric acid concentrations in the urine and the serum were determined by the enzyme method. On the other hand, creatine concentrations in the urine and the serum were determined by a Jaffe's method to obtain the fractional excretion of uric acid. Percent of uric acid excretion was calculated by dividing the value of fractional excretion in the test group by that in the control group. The results obtained are shown in Table 2 below.

TABLE 2

| Test Compound | Number of Animal | Dose (mg/Kg) | % of Uric Acid Excretion |
|---|---|---|---|
| (a) | 7 | 100 | 136** |
| (b) | 7 | 100 | 66** |
| (c) | 7 | 100 | 36** |
| (d) | 7 | 100 | 56** |
| (e) | 7 | 100 | 39** |
| Tienilic acid | 7 | 200 | 38** |

*$P < 0.05$ vs. Control
**$P < 0.01$ vs. Control

As is apparent from the Table 2, the compounds of the present invention exhibited superior uricosuric activity to tienilic acid.

(3) Antihypertensive Activity:

Four-week-old male rats weighing 120 to 150 g were subcutaneously injected with DOCA (desoxycorticosterone acetate) and fed on a 1% saline solution to cause hypertension in accordance with the method of Seyle, et al. as described in *American Heart Journal*, Vol. 37, 1009 (1949). The test compound was orally administered to the hypertensive rats once a day for 4 weeks. The blood pressure of the animal was measured by a tail cuff method every one week from the start of the administration. The results obtained are shown in Table 3 below.

TABLE 3

| Test Compound | Number of Animal | Dose (mg/Kg) | Antihypertensive Activity ($\Delta$mmHg) | | |
|---|---|---|---|---|---|
| | | | After 1 Week | After 2 Weeks | After 3 Weeks |
| (a) | 7 | 100 | 13.7* | 37.0** | 49.0** |
| (b) | 7 | 100 | 10.0** | 17.9** | 15.0 |
| (c) | 7 | 100 | 13.6* | 20.7** | 29.3** |
| (d) | 7 | 100 | 12.1 | 14.3* | 15.7 |
| (e) | 7 | 100 | 6.2 | 28.7** | 39.4** |
| Tienilic acid | 7 | 300 | 23.6** | 35.0 | 44.3 |

*$P < 0.05$ vs. Control
**$P < 0.01$ vs. Control

In Table 3, antihypertensive activity ($\Delta$mmHg) was obtained by subtracting the systolic pressure of the test group from that of the control group.

As is apparent from the Table 3, the compounds of the present invention exhibited higher antihypertensive activity than tienilic acid.

As is apparent from the above results, the compound of the present invention exhibited excellent uricosuric, diuretic and antihypertensive activities as compared with the representative known compound.

The compound of the present invention has a low toxicity, and the acute toxicity ($LD_{50}$) of typical compounds of formula (I) is shown in the following Table 4.

TABLE 4

| Test Compound | $LD_{50}$ (mg/Kg P.O. in Rats) |
|---|---|
| (a) | 1021 |
| (b) | 936 |
| (c) | 1412 |

The compound of the present invention can be administered orally or parenterally. The oral dosage level of the compound of the present invention is usually in the range of from 10 to 200 mg per adult human (about 50 Kg body weight) per day.

The pharmaceutical preparations containing the compound of the present invention include tablets, capsules, powder, granules and the like. The preparations can be produced by conventional techniques using appropriate additives such as lactose, corn starch, crystalline cellulose, polyvinyl alcohol, carboxymethyl cellulose calcium, magnesium stearate, talc and the like.

The present invention is now illustrated in greater detail by the following Reference Examples and Examples but it should be understood that the present invention is not limited thereto.

REFERENCE EXAMPLE 1

(1) Synthesis of 1-(2-chloro-6-hydroxy-4-methoxy)phenyl-2-(2-methylphenyl)-1-ethanone In 4 l of 1,2-dichloroethane were suspended 390 g of anhydrous aluminum chloride and 38 g of zinc chloride, and the suspension was stirred for 30 minutes at 0° C. To the resulting solution was added 400 ml of a 1,2-dichloroethane solution containing 483 g of 5-chloro-1,3-dimethoxybenzene. To the mixture was added dropwise 400 ml of a 1,2-dichloroethane solution containing 470 g of 2-methylphenylacetyl chloride over a period of 1.5 hours while maintaining the temperature at −10° C. by cooling with ice and sodium chloride. After the addition, the reaction mixture was stirred at room temperature for 1 hour and then at 70° C. for an additional one hour. The reaction mixture was poured into ice-water containing hydrochloric acid and extracted with chloroform. The chloroform layer was washed with water, dried over sodium sulfate, and distilled under reduced pressure to remove the solvent. The residue was recrystallized from benzene to obtain 380 g of the entitled compound having a melting point of 107° to 108° C.

(2) Synthesis of 5-chloro-7-methoxy-3-(2-methylphenyl)-4-oxo-4H-1-benzopyran

In one liter of 1,4-dioxane was dissolved 303 g of the above obtained compound, and 1.3 l of ethyl formate was added thereto. To the mixture was added 113 g of 60% sodium hydride in small portions under ice-cooling while stirring. The mixture was heated at 40° C. for 3 hours. The reaction mixture was poured into ice-water containing hydrochloric acid and extracted with chloroform. The chloroform layer was washed with water, dried over sodium sulfate, and distilled under reduced pressure to remove the solvent. The residue was heated at 160° C. under reduced pressure for 1 hour, followed by recrystallization from benzene to obtain 250 g of the entitled compound having a melting point of 159° to 160° C.

(3) Synthesis of 5-chloro-7-hydroxy-3-(2-methylphenyl)-4-oxo-4H-1-benzopyran

In 2.5 l of benzene was suspended 225 g of the above obtained compound, and 300 g of anhydrous aluminum chloride was added thereto, followed by refluxing for 1 hour. After cooling, 1.5 l of petroleum ether was added to the reaction mixture, followed by allowing to stand overnight. The organic layer was removed by decantation. Ice-water was added to the residue, and the mixture was vigorously agitated. The insoluble crystals were collected by filtration, washed with hot water, and dried to obtain 210 g of the entitled compound having a melting point of above 290° C.

REFERENCE EXAMPLES 2 to 12

In the same manner as in Reference Example 1, the following compounds were prepared.

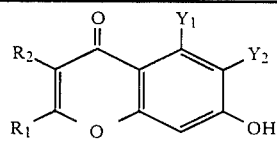

| Reference Example No. | $R_1$ | $R_2$ | $Y_1$ | $Y_2$ | Melting Point (°C.) |
|---|---|---|---|---|---|
| 2 | H | phenyl | Cl | H | >290 |
| 3 | H | phenyl | F | H | |
| 4 | H | 3-methylphenyl | $CH_3$ | H | 247–248 |
| 5 | H | 2-chlorophenyl | $CH_3$ | H | 228–230 |
| 6 | H | 2-fluorophenyl | Cl | H | |
| 7 | H | benzyl | Cl | H | 297–300 |
| 8 | H | 4-hydroxyphenyl | Cl | H | >300 |
| 9 | H | 2-hydroxyphenyl | Cl | H | |
| 10 | H | 4-hydroxy-3-methylphenyl | Cl | H | 290–292 |
| 11 | H | 2-chlorobenzyl | Cl | H | 170–172 |
| 12 | H | 2-phenylethyl | Cl | H | 240–241 (decomp.) |

REFERENCE EXAMPLE 13

(1) Synthesis of 1-(2-chloro-6-hydroxy-4-methoxy)phenyl-3-methyl-1-butanone

The entitled compound was prepared in the same manner as in Reference Example 1-1).

(2) Synthesis of 5-chloro-3-isopropyl-7-methoxy-4-oxo-4H-1-benzopyran

In 230 ml of ethyl formate was dissolved 44 g of the above obtained compound, and 12.4 g of sodium wire was added to the solution, followed by stirring at room temperature for 3 hours. After sodium was completely dissolved, the reaction mixture was heated up to 60° C. and stirred at that temperature for 2 hours. The reaction mixture was poured into ice-water containing hydrochloric acid, and the organic layer was separated. The aqueous layer was extracted with chloroform. The organic layer and the chloroform layer were combined, washed successively with water and a saturated sodium chloride aqueous solution, and dried over sodium sulfate. The solvent was removed by distillation under reduced pressure, and the residue was heated at 160° C. for 1 hour under reduced pressure. Recrystallization of the residue from benzene gave 17.6 g of the entitled compound having a melting point of 177° to 179° C.

(3) Synthesis of 5-chloro-3-isopropyl-7-hydroxy-4-oxo-4H-1-benzopyran

The entitled compound was prepared in the same manner as in Reference Example (1-3) from the compound obtained in (2) above. Melting Point: 256°–260° C. (with decomposition).

REFERENCE EXAMPLE 14

5-Chloro-3-cyclopentyl-7-hydroxy-4-oxo-4H-1-benzopyran was prepared in the same manner as in Reference Example 13. Melting Point: 282°–284° C.

REFERENCE EXAMPLE 15

(1) Synthesis of 1-(2,3-dichloro-6-hydroxy-4-methoxy)-phenyl-2-phenyl-1-ethanone The entitled compound was prepared in the same manner as in Reference Example (1-1). Melting Point: 179°–180° C.

(2) Synthesis of 5,6-dichloro-7-methoxy-4-oxo-3-phenyl-4H-1-benzopyran

A mixture comprising 28.4 g of the above compound obtained in (1) above, 173 ml of ethyl orthoformate, 230 ml of dried pyridine, and 9 ml of dried piperidine was refluxed for 4 hours. The reaction mixture was poured into ice-water containing hydrochloric acid, and the insoluble material was extracted with dichloromethane. The organic layer was washed with water and dried over sodium sulfate. The solvent was removed by distillation under reduced pressure, and the residue was subjected to silica gel column chromatography. The resulting crude crystals were recrystallized from benzene to obtain 14.3 g of the entitled compound having a melting point of 216°–218° C.

(3) Synthesis of 5,6-dichloro-7-hydroxy-4-oxo-3-phenyl-4H-1-benzopyran

The entitled compound was prepared from the compound obtained in (2) above in the same manner as in Reference Example (1-3). Melting Point: above 290° C.

REFERENCE EXAMPLES 16 TO 21

In the same manner as in Reference Example 15, the following compounds were prepared.

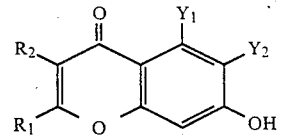

| Reference Example No. | R₁ | R₂ | Y₁ | Y₂ | Melting Point (°C.) |
|---|---|---|---|---|---|
| 16 | H | phenyl | CH₃ | H | 252–253 |
| 17 | H | 4-chlorophenyl | Cl | H | >290 |
| 18 | H | 4-fluorophenyl | Cl | H | >290 |
| 19 | H | phenyl | Cl | CH₃ | >300 |
| 20 | H | 3-chlorophenyl | Cl | H | 288–289 |
| 21 | H | phenyl | I | H | 268–270 |

REFERENCE EXAMPLE 22

(1) Syntheis of 5-chloro-7-methoxy-2-methyl-3-(2-methylphenyl)-4-oxo-4H-1-benzopyran In 150 ml of dried pyridine was dissolved 17.6 g of 1-(2-chloro-6-hydroxy-4-methoxy)phenyl-2-(2-methylphenyl)-1-ethanone prepared in Reference Example (1-1), and 6.5 ml of dried piperidine and 75 g of ethyl orthoacetate were added to the solution, followed by refluxing for 7 hours. After cooling, the reaction mixture was poured into dilute hydrochloric acid and extracted with ethyl acetate. The organic layer was dried over sodium sulfate and distilled under reduced pressure to remove the solvent. The residue was subjected to silica gel column chromatography. Recrystallization of the resulting crude crystals from ethanol gave 3.0 g of the entitled compound having a melting point of 138° to 140° C.

(2) Synthesis of 5-chloro-7-hydroxy-2-methyl-3-(2-methylphenyl)-4-oxo-4H-1-benzopyran The entitled compound was prepared from the compound obtained in (1) above in the same manner as in Reference Example (1-3).

REFERENCE EXAMPLE 23

In the same manner as in Reference Example 22, 5-chloro-7-hydroxy-2-methyl-3-phenyl-4-oxo-4H-1-benzopyran was prepared. Melting Point: above 300° C.

REFERENCE EXAMPLE 24

(1) Synthesis of 2-chloro-6-hydroxy-4-methoxyacetophenone

To 460 ml of 1,2-dichloroethane were added 46.4 g of ground anhydrous aluminum chloride and 4.74 g of zinc chloride, followed by stirring for 30 minutes. Under ice-cooling, a solution of 60 g of 5-chloro-1,3-dimethoxybenzene in 150 ml of 1,2-dichloroethane was added thereto. To the reaction mixture was added dropwise 27.3 g of acetyl chloride over a period of 30 minutes while maintaining the temperature at −10° to −15° C. After the addition, the stirring was continued at 0° C. for 2 hours and then at 70° C. for an additional 1.5 hours. The reaction mixture was allowed to cool, poured into ice-water containing hydrochloric acid, and extracted with chloroform. The chloroform layer was dried over sodium sulfate, and concentrated under reduced pressure. The residue was crystallized from petroleum ether to obtain 45.0 g of the entitled compound containing 4-chloro-2-hydroxy-6-methoxyacetophenone as a by-product.

(2) Synthesis of 1-(2-chloro-6-hydroxy-4-methoxy)phenyl-3-dimethylamino-2-propen-1-one In 44.0 ml of dimethylformamide dimethylacetal was dissolved 44.0 g of the above obtained compound, and the solution was stirred at 60° C. for 30 minutes. Excess of the dimethylformamide dimethylacetal was removed by distillation under reduced pressure, and the residue was purified by silica gel column chromatography to obtain 26 g of crude crystals of the entitled compound.

(3) Synthesis of 3-bromo-5-chloro-7-methoxy-4-oxo-4H-1-benzopyran

In 260 ml of chloroform was dissolved 26 g of the above obtained compound. A solution of 5.24 ml of bromine in 5 ml of chloroform was added dropwise to the solution under cooling to −10° to −15° C. while stirring. The stirring was continued at 0° C. for an additional 30 minutes. Water was added thereto, followed by stirring, and the reaction mixture was extracted with chloroform. The chloroform layer was dried over sodium sulfate and concentrated under reduced pressure. The resulting residue was recrystallized from benzene to obtain 8.4 g of the entitled compound having a melting point of 176°–177° C.

(4) Synthesis of 5-chloro-7-methoxy-4-oxo-3-piperidinyl-4H-1-benzopyran

In 20 ml of hexamethylphosphoric triamide was dissolved 2.8 g of the above obtained compound, and 5.7 ml of piperidine was added thereto, followed by stirring at room temperature for 2 days. The reaction mixture was poured into ice-water, and the precipitated crystals were collected by filtration. The resulting crude crystals were subjected to silica gel column chromatography to obtain 2.8 g of the entitled compound having a melting point of 122°–125° C.

(5) Synthesis of 5-chloro-7-hydroxy-4-oxo-3-(1-piperidinyl)-4H-1-benzopyran hydrobromide In 130 ml of 48 wt % hydrobromic acid was suspended 2.8 g of the above obtained compound, and the suspension was stirred at 150° C. for 6 hours. The reaction mixture was cooled, and the precipitated crystals were collected by filtration, washed with water, and dried to yield 3.3 g of the entitled compound.

EXAMPLE 1

Synthesis of ethyl {[5-chloro-3-(2-methylphenyl)-4-oxo-4H-1-benzopyran-7-yl]oxy}acetate In 1 l of acetone was suspended 114 g of 5-chloro-7-hydroxy-3-(2-methylphenyl)-4-oxo-4H-1-benzopyran, and 60.4 g of anhydrous potassium carbonate and 73.0 g of ethyl bromoacetate were added thereto, followed by refluxing for 1.5 hours. After cooling, the insoluble material was removed by filtration, and the filtrate was concentrated under reduced pressure. Recrystallization of the residue from ethanol gave 132 g of the entitled compound having a melting point of 122° to 123° C.

EXAMPLES 2 TO 24

In the same manner as in Example 1, the following compounds were prepared.

| Example No. | $R_1$ | $R_2$ | $Y_1$ | $Y_2$ | Melting Point (°C.) |
|---|---|---|---|---|---|
| 2 | H | phenyl | Cl | H | 130–131 |
| 3 | H | phenyl | Cl | Cl | |
| 4 | H | phenyl | $CH_3$ | H | 127–129 |
| 5 | H | 4-chlorophenyl | Cl | H | |
| 6 | H | $-CH(CH_3)_2$ | Cl | H | |
| 7 | H | 4-fluorophenyl | Cl | H | |
| 8 | H | phenyl | F | H | 109–110 |
| 9 | H | cyclopentyl | Cl | H | |
| 10 | H | phenyl | Cl | $CH_3$ | |
| 11 | H | 2-chlorophenyl | Cl | H | |
| 12 | H | 3-methylphenyl | $CH_3$ | H | 99–100 |

-continued

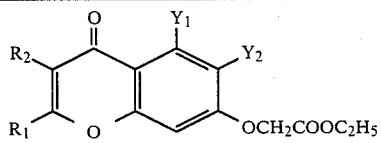

| Example No. | R₁ | R₂ | Y₁ | Y₂ | Melting Point (°C.) |
|---|---|---|---|---|---|
| 13 | H | (2-chlorophenyl) | CH₃ | H | |
| 14 | H | (2-fluorophenyl) | Cl | H | 117–118 |
| 15 | H | —CH₂—(phenyl) | Cl | H | 166–168 |
| 16 | H | (4-hydroxyphenyl) | Cl | H | 186–187 |
| 17 | H | (3-hydroxyphenyl) | Cl | H | 142–143 |
| 18 | H | (4-hydroxy-3-methylphenyl) | Cl | H | 188–190 |
| 19 | H | —CH₂—(2-chlorophenyl) | Cl | H | 123–125 |
| 20 | H | —CH₂CH₂—(phenyl) | Cl | H | 114–115 |
| 21 | H | (phenyl) | I | H | 155–156 |
| 22 | CH₃ | (phenyl) | Cl | H | 122–123 |

-continued

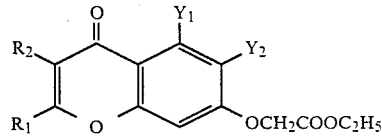

| Example No. | R₁ | R₂ | Y₁ | Y₂ | Melting Point (°C.) |
|---|---|---|---|---|---|
| 23 | CH₃ | (2-methylphenyl) | Cl | H | 99–100 |
| 24 | H | —N(piperidinyl) | Cl | H | 109–111 |

EXAMPLE 25

Synthesis of ethyl {[4-oxo-3-phenyl-5-trifluoromethyl-4H-1-benzopyran-7-yl]oxy}acetate In a stainless steel-made reaction tube were placed 9.5 g of a copper powder and 30 ml of hexamethylphosphoric triamide, and 6 ml of iodotrifluoromethyl was added thereto in a closed system while cooling with dry ice-acetone. The mixture was heated to 125° C. and stirred at that temperature for 2.5 hours. After cooling, 3.5 g of ethyl {[5-iodo-4-oxo-3-phenyl-4H-1-benzopyran-7-yl]oxy}acetate was added thereto. Nitrogen gas was introduced in the atmosphere, and the mixture was stirred at 45° C. for 12 hours. The reaction mixture was poured into 500 ml of a benzene-ethyl acetate mixture (1:1 by volume), and 500 ml of ice-water was then added thereto, followed by stirring for 30 minutes. The precipitate thus formed was removed by filtration through Celite, and the filtrate was washed with water and dried over sodium sulfate. The solvent was removed by distillation under reduced pressure, and the residue was subjected to silica gel column chromatography. Recrystallization of the resulting crude crystals from ethanol gave 2.65 g of the entitled compound having a melting point of 139° to 140° C.

EXAMPLE 26

Synthesis of ethyl {[5-chloro-3-(4-methoxyphenyl)-4-oxo-4H-1-benzopyran-7-yl]oxy}acetate In 150 ml of acetone was dissolved 5.5 g of ethyl {[5-chloro-3-(4-hydroxyphenyl)-4-oxo-4H-1-benzopyran-7-yl]oxy}acetate under heating, and 4.8 g of anhydrous potassium carbonate was added thereto. To the solution was added 3.4 ml of methyl iodide, followed by refluxing for 2 hours. After cooling, the solvent was removed by distillation under reduced pressure. Water was added to the residue, and the insoluble material was extracted with ethyl acetate. The organic layer was dried over sodium sulfate and distilled under reduced pressure to remove the solvent. The residue was recrystallized from ethanol-chloroform to obtain 5.0 g of the entitled compound having a melting point of 121° to 122° C.

EXAMPLES 27 AND 28

In the same manner as in Example 26, the following compounds were prepared.

![Structure with R1, R2, Y1, Y2, OCH2COOC2H5]

| Example No. | R1 | R2 | Y1 | Y2 | Melting Point (°C.) |
|---|---|---|---|---|---|
| 27 | H | (2-methoxyphenyl) CH3O- | Cl | H | 135–136 |
| 28 | H | (4-methoxy-3-methylphenyl) | Cl | H | — |

EXAMPLE 29

Synthesis of {[5-chloro-3-(2-methylphenyl)-4-oxo-4H-1-benzopyran-7-yl]oxy}acetic acid In 1.2 l of ethanol was suspended 132 g of ethyl {[5-chloro-3-(2-methylphenyl)-4-oxo-4H-1-benzopyran-7-yl]oxy}acetate, and 0.53 l of a 1N sodium hydroxide aqueous solution was slowly added dropwise to the suspension at room temperature, followed by stirring at room temperature for 3 hours. The insoluble material was removed by filtration, and the filtrate was acidified with hydrochloric acid while ice-cooling and stirring. The stirring was continued at room temperature overnight. The precipitated crystals were collected by filtration, washed with water, and dried to obtain 105 g of the entitled compound having a melting point of 191° to 192° C.

NMR δppm (DMSO-$d_6$, TMS):
2.16 (3H, s), 4.94 (2H, s),
7.1–7.3 (4H, m), 8.20 (1H, s)

EXAMPLES 30 TO 53

In the same manner as in Example 29, the following compounds were prepared.

![Structure with R1, R2, Y1, Y2, OCH2COOH]

| Example No. | R1 | R2 | Y1 | Y2 | Melting Point (°C.) | NMR δppm (DMSO—$d_6$, TMS) |
|---|---|---|---|---|---|---|
| 30 | H | phenyl | Cl | H | 242–245 | 4.86(2H,s), 7.08(2H,s), 7.2–7.6(5H,m), 8.26(1H,s) |
| 31 | H | phenyl | Cl | Cl | 289–290 (decomp.) | 5.0(2H,s), 7.2–7.6(6H,m), 8.33(1H,s) |
| 32 | H | phenyl | CH3 | H | 208–210 | 2.72(3H,s), 4.80(2H,s), 6.88(1H,d), 6.86(1H,d), 7.2–7.6(5H,m), 8.20(1H,s) |
| 33 | H | 4-chlorophenyl | Cl | H | 254–257 | 4.93(2H,s), 7.16(2H,s), 7.4–7.7(4H,m), 8.40(1H,s) |
| 34 | H | phenyl | CF3 | H | 259–261 | 4.95(2H,s), 7.1–7.6(7H,m), 8.35(1H,s) |
| 35 | H | —CH(CH3)2 | Cl | H | 172–174 | 1.14(6H,d), 2.6–3.2(1H,m), 4.86(2H,s), 7.02(2H,s), 7.93(1H,s) |

-continued
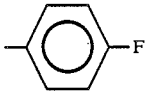
| Example No. | R₁ | R₂ | Y₁ | Y₂ | Melting Point (°C.) | NMR δppm (DMSO—d₆, TMS) |
|---|---|---|---|---|---|---|
| 36 | H |  -F | Cl | H | 265–267 | 4.92(2H,s), 7.17(2H,s), 7.25(2H,dd), 7.58(2H,dd), 8.39(1H,s) |
| 37 | H |  | F | H | 169–170 | 4.86(2H,s), 6.87(1H,dd), 6.95(1H,m), 7.20–7.60(5H,m), 8.25(1H,s) |
| 38 | H | 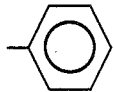 | Cl | H | 197–199 | 1.2–2.2(8H,m), 2.7–3.2(1H,m), 4.89(2H,s), 7.08(2H,s), 8.04(1H,s) |
| 39 | H | 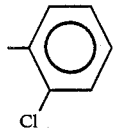 | Cl | CH₃ | >300 | 2.33(3H,s), 4.93(2H,s), 7.11(1H,s), 7.20–7.60(5H,m), 8.31(1H,s) |
| 40 | H | 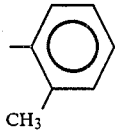 Cl | Cl | H | 193–195 | 4.94(2H,s), 7.20(2H,s), 7.3–7.7(4H,m), 8.32(1H,s), |
| 41 | H | 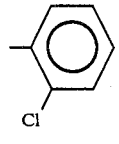 CH₃ (with CH₃) | CH₃ | H | 195–196 | 2.20(3H,s), 2.79(3H,s), 4.70(2H,s), 6.79(2H,s), 7.10–7.40(4H,m), 7.74(1H,s) (CDCl₃ in place of DMSO—d₆) |
| 42 | H | 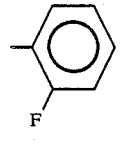 Cl | CH₃ | H | 198–200 | 2.72(3H,s), 4.85(2H,s), 6.90(1H,s), 6.96(1H,s), 7.30–7.65(4H,m), 8.22(1H,s) |
| 43 | H | 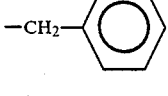 F | Cl | H | 171–173 | 4.90(2H,s), 7.13(2H,s), 7.10–7.50(4H,m), 8.30(1H,s) |
| 44 | H | —CH₂— 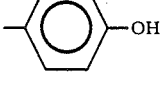 | Cl | H | 156–159 | 3.62(2H,s), 4.84(2H,s), 7.01(2H,s), 7.20(5H,s), 8.06(1H,s) |
| 45 | H | 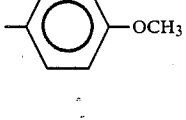 —OH | Cl | H | >300 | 4.86(2H,s), 6.76(2H,d), 7.04(2H,s), 7.20(5H,s), 8.14(1H,s) |
| 46 | H | —OCH₃ (phenyl) | Cl | H | 240–244 | 3.75(3H,s), 4.86(2H,s), 6.92(2H,dd), 7.06(2H,s), 7.40(2H,d), 8.21(1H,s) |

-continued

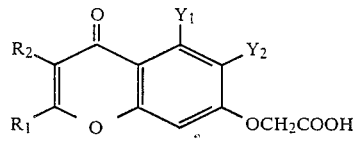

| Example No. | R₁ | R₂ | Y₁ | Y₂ | Melting Point (°C.) | NMR δppm (DMSO—d₆, TMS) |
|---|---|---|---|---|---|---|
| 47 | H | (2-methoxyphenyl) CH₃O-C₆H₄- | Cl | H | 184–185 | 3.72(3H,s), 4.87(2H,s), 7.07(2H,s), 6.80–7.50(4H,m), 8.10(1H,s) |
| 48 | H | (methyl, methoxyphenyl) CH₃-, -OCH₃ | Cl | H | 221–223 | 2.12(3H,s), 3.75(3H,s), 4.87(2H,s), 6.73(1H,d), 6.76(1H,s), 7.02(1H,d), 7.07(2H,s), 8.05(1H,s) |
| 49 | H | —CH₂—(2-chlorophenyl) | Cl | H | 170–172 | 3.75(2H,s), 4.91(2H,s), 7.12(2H,s), 7.2–7.6(4H,m), 8.05(1H,s) |
| 50 | H | —(CH₂)₂—C₆H₅ | Cl | H | 157–158 | 2.5–2.8(4H,m), 4.85(2H,s), 6.95–7.06(2H), 7.16(5H,s), 7.90(1H,s) |
| 51 | CH₃ | C₆H₅ | Cl | H | 184–186 | 2.17(3H,s), 4.87(2H,s), 7.03(2H,s), 7.10–7.50(5H,m) |
| 52 | CH₃ | (3-methylphenyl) | Cl | H | 194–196 | 2.09(6H,s), 4.88(2H,s), 7.06(2H,s), 7.00–7.33(4H,m) |
| 53 | H | —N(piperidinyl) | Cl | H | 210–220 (hydrochloride) | 1.4–2.0(6H,m), 3.1–3.4(4H,m), 4.71(2H,s), 6.66(1H,d), 7.01(1H,d), 7.80(1H,s) |

EXAMPLE 54

Synthesis of {[5-chloro-3-(2-hydroxyphenyl)-4-oxo-4H-1-benzopyran-7-yl]oxy}acetic acid In 100 ml of dried dichloromethane was dissolved 1.7 g of ethyl {[5-chloro-3-(2-hydroxyphenyl)-4-oxo-4H-1-benzopyran-7-yl]oxy}acetate, and the solution was cooled with dry ice-acetone. Three milliliters of boron tribromide were added to the cooled solution in small portions, and the resulting mixture was refluxed for 3 hours. After cooling, the solvent was removed by distillation under reduced pressure, and to the residue was added dilute hydrochloric acid. The precipitated crystals were collected by filtration, washed with water, air-dried, and recrystallized from ethanol to obtain 1.0 g of the entitled compound having a melting point of 188°–189° C. (with decomposition).

NMR δppm (DMSO-d₆, TMS):
4.87 (2H, s), 6.65–6.90 (2H, m), 7.07 (2H, s), 6.95–7.30 (2H, m), 8.10 (1H, s), 9.22 (1H, s)

EXAMPLE 55

Synthesis of {[5-chloro-2,3-dihydro-4-oxo-3-phenyl-4H-1-benzopyran-7-yl]oxy}acetic acid One gram of {[5-chloro-4-oxo-3-phenyl-4H-1-benzopyran-7-yl]oxy}acetic acid was dissolved in 200 ml of methanol while heating, and 50 mg of platinum (IV) oxide was added to the solution. After an equimole of hydrogen was absorbed, the platinum catalyst was removed by filtration. The methanol in the filtrate was removed by distillation, and the residue was recrystallized from chloroform to obtain 0.4 g of the entitled compound having a melting point of 171° to 173° C.

NMR δppm (DMSO-d$_6$, TMS):
4.11 (1H, dd), 4.6–5.0 (4H, m), 6.58 (1H, d), 6.75 (1H, d), 7.30 (5H br. s)

EXAMPLE 56

(1) Synthesis of {[5-chloro-3-(2-chlorophenyl)-4-oxo-4H-1-benzopyran-7-yl]oxy}acetonitrile In 50 ml of acetone was dissolved 1.4 g of 5-chloro-3-(2-chlorophenyl)-7-hydroxy-4-oxo-4H-1-benzopyran, and 0.7 g of anhydrous potassium carbonate, 0.38 g of chloroacetonitrile and 0.15 g of potassium iodide were added to the solution, followed by refluxing for 8 hours. Water was added to the reaction mixture, and the precipitated crystals were collected by filtration. Recrystallization of the crystals from ethanol gave 1.4 g of the entitled compound having a melting point of 174° to 175° C.

(2) Synthesis of {[5-chloro-3-(2-chlorophenyl)-4-oxo-4H-1-benzopyran-7-yl]oxymethyl}tetrazole In 60 ml of dimethylformamide was dissolved 1.2 g of {[5-chloro-3-(2-chlorophenyl-4-oxo-4H-1-benzopyran-7-yl]oxy}acetonitrile. To the solution were added 0.26 g of sodium azide and 0.21 g of ammonium chloride, followed by allowing the mixture to react at 100° to 110° C. for 12 hours. The reaction mixture was poured into ice-water containing hydrochloric acid, and the precipitated crystals were collected by filtration, washed with water, and dried to obtain 1.1 g of the entitled compound having a melting point of 192° to 195° C.

NMR δppm (DMSO-d$_6$, TMS):
5.64 (2H, s), 7.16–7.56 (6H, m), 8.25 (1H, s)

While the invention has been described in detail and with reference to specific embodiments thereof, it will be apparent to one skilled in the art that various changes and modifications can be made therein without departing from the spirit and scope thereof.

What is claimed is:

1. A benzopyran derivative represented by the formula

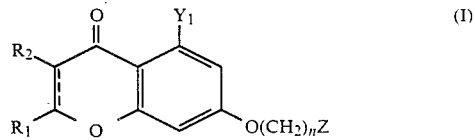

wherein;
$R_1$ represents a hydrogen atom or a lower alkyl group;
$R_2$ represents a lower alkyl group, a cycloalkyl group, a phenyl group which may have one or more substituents selected from the group consisting of halogen atom, lower alkyl group, lower alkoxy group and hydroxyl group, or a phenylalkyl group;
$Y_1$ represents a halogen atom or a trihalomethyl group;
Z represents a carboxyl group, a lower alkoxycarbonyl group;
n represents an integer of from 1 to 6; and the bond=== between the 2- and 3-positions represents a single bond or a double bond; and pharmaceutically acceptable salts thereof.

2. A benzopyran derivative and pharmaceutically acceptable salts thereof as claimed in claim 1, wherein $R_2$ represents a phenyl group which may be substituted with a halogen atom, a lower alkyl group or a lower alkoxy group, $R_1$ represents a hydrogen atom, $Y_1$ represents a halogen atom, n represents 1, and Z represents a carboxyl group.

3. [(5-Chloro-4-oxo-3-phenyl-4H-1-benzopyran-7-yl)oxy]acetic acid and pharmaceutically acceptable salts thereof according to claim 1.

4. [5-Chloro-3-(2-chlorophenyl)-4-oxo-4H-1-benzopyran-7-yl]oxyacetic acid and pharmaceutically acceptable salts thereof according to claim 1.

5. [5-Chloro-3-(2-methylphenyl)-4-oxo-4H-1-benzopyran-7-yl]oxyacetic acid and pharmaceutically acceptable salts thereof according to claim 1.

6. [(3-Benzyl-5-chloro-4-oxo-4H-1-benzopyran-7-yl)oxy]acetic acid and pharmaceutically acceptable salts thereof according to claim 1.

* * * * *